US012004778B2

(12) United States Patent
Bennett

(10) Patent No.: US 12,004,778 B2
(45) Date of Patent: Jun. 11, 2024

(54) SPINAL HOOK

(71) Applicant: Phoenix Children's Hospital, Inc., Phoenix, AZ (US)

(72) Inventor: David Bennett, Gilbert, AZ (US)

(73) Assignee: PHOENIX CHILDREN'S HOSPITAL, INC, Phoenix, AZ (US)

(*) Notice: Subject to any disclaimer, the term of this patent is extended or adjusted under 35 U.S.C. 154(b) by 0 days.

(21) Appl. No.: 17/834,732

(22) Filed: Jun. 7, 2022

(65) Prior Publication Data

US 2022/0395296 A1 Dec. 15, 2022

Related U.S. Application Data

(60) Provisional application No. 63/209,852, filed on Jun. 11, 2021.

(51) Int. Cl.
*A61B 17/70* (2006.01)

(52) U.S. Cl.
CPC ...... *A61B 17/7035* (2013.01); *A61B 17/7034* (2013.01)

(58) Field of Classification Search
CPC ............ A61B 17/7032; A61B 17/7056; A61B 17/7035; A61B 17/7037
USPC ......................................................... 606/276
See application file for complete search history.

(56) References Cited

U.S. PATENT DOCUMENTS

| 5,170,662 A * | 12/1992 | Brault | G01L 5/133 73/112.04 |
|---|---|---|---|
| 5,312,402 A * | 5/1994 | Schlapfer | A61B 17/6466 606/267 |
| 5,688,274 A * | 11/1997 | Errico | A61B 17/7056 606/272 |
| 2002/0040222 A1* | 4/2002 | Hashimoto | A61B 17/7022 606/330 |
| 2003/0187437 A1* | 10/2003 | Ginsburg | A61B 17/7056 606/907 |
| 2014/0200617 A1* | 7/2014 | Farris | A61B 17/7032 606/278 |
| 2014/0277155 A1* | 9/2014 | Barrus | A61B 17/7032 606/276 |
| 2014/0303675 A1* | 10/2014 | Mishra | A61B 17/7002 606/279 |
| 2015/0119941 A1* | 4/2015 | Daniels | A61B 17/7052 606/276 |
| 2015/0190178 A1* | 7/2015 | McCarthy | A61B 17/7049 606/279 |
| 2015/0230828 A1* | 8/2015 | Barrus | A61B 17/7032 606/279 |

(Continued)

FOREIGN PATENT DOCUMENTS

EP 2036510 A1 * 3/2009 ........... A61B 17/701

*Primary Examiner* — Jan Christopher L Merene

(74) *Attorney, Agent, or Firm* — Messner Reeves LLP

(57) ABSTRACT

A hook anchor for anchoring a fixation rod to a bone is disclosed. The hook anchor includes a hook body shaped in a curve of diminishing radius and a locking mechanism. The locking mechanism is to securely fix the hook anchor to the fixation rod. The curve of diminishing radius may be the shape of at least a portion of a Fibonacci curve. The bone can include at least one of a rib, a pelvis, and a vertebra. The hook body can be configured to engage with at least one of a spinous process a transverse process, and a pedicle of the vertebra.

14 Claims, 20 Drawing Sheets

(56) References Cited

U.S. PATENT DOCUMENTS

2016/0058478 A1* 3/2016 Agarwal ............ A61B 17/7032
                                                    606/270
2020/0194946 A1* 6/2020 Garcia Beard ...... H01R 13/506

* cited by examiner

SPINAL HOOK

CROSS-REFERENCES TO RELATED APPLICATIONS

This application claims priority to and incorporates by reference U.S. Provisional Patent Application No. 63/209,852 entitled "SPINAL HOOK" and filed on Jun. 11, 2021.

STATEMENT REGARDING FEDERALLY SPONSORED RESEARCH

Not Applicable.

FIELD OF THE INVENTION

This disclosure relates generally to spinal fixation devices and, more specifically, to hook devices configured to engage with a portion of a vertebra, pelvic bone, rib, or other bone process.

BACKGROUND OF THE INVENTION

The human spine consists of a number of vertebrae separated by intervertebral disks. The spine sits upon the pelvis. A number of muscles, ligaments, and tendons interconnect between the vertebrae and pelvis to provide support to the spine and enable movement thereof. Each vertebra and disc of the spine includes enclosed central openings that form the vertebral canal. The spinal cord projects through the vertebral canal. Spinal fluid circulates through the vertebral canal.

In some instances, the spine may be subject to abnormal development or curvature due to diseases, such as infections, tumors, scoliosis, or arthritic disorders, injury, or trauma, such as puncturing or slippage of discs, bone fractures, or bone displacement, or genetic predisposition. Improper curvature of the spine may lead to significant body deformities, which can result in serious symptoms, such as pain, weakness, and, ultimately, pulmonary and cardia problems.

Spinal fixation systems can be used in orthopedic surgery to influence the position and spatial relationships between various vertebrae of the spine and the pelvis. Such fixation systems typical includes a rigid rod that extends along a length of the spine. The rod is fixed to the spine and, optionally, the pelvis via a number of anchoring devices to securely hold the rod in place. The rod is arranged with a predetermined curvature so that when the rod is fixed to the spine and, optionally, pelvis, the rod's curvature operates to apply a force to the various vertebrae to which the rod is fixed.

In some cases, the curvature of the rod may match that of the patient's spine and the fixation system may operate to primarily hold the vertebrae in place. But in the case of spinal curvature correction, the curvature of the fixation system's rods cause the anchoring members to apply to force to the vertebrae to correct their positions with respect to other vertebrae of the spine and the pelvis. During a treatment regimen for a particular spinal curvature deformation, a number of different anchoring rods may be used over time with incrementally different curvature to gradually correct a spinal curvature malformation.

The curved rods of a spinal fixation system may be anchored to specific portions of the spine and pelvis using a number of different anchoring devices, such as hooks, bolts, wires, and screws. Because each vertebra varies in shape and size, a variety of anchoring devices may be used with the same curved rod to anchor the rod to a particular portion of the spine or pelvic bone. Pedicle hook assemblies, for example, have a shape and size that is configured to engage spinal pedicle bone structures. Conventionally, pedicle hooks include a blade portion that is adapted to partially engage bone structures, such as the vertebral transverse process or spinous process and a shank portion having a rod-receiving element, usually in the form of a U-shaped channel, to engage the spinal fixation system rod.

During conventional use of a spinal fixation system, the ends of the spinal fixation system rod are each loosely secured to one or more pedicle hook anchors. The blade portion of each pedicle hook anchor is then moved into engagement with a pedicle bone of the vertebrae, Once properly positioned, the fixation rod is locked in place to the pedicle hook anchors by tightening a locking mechanism to securely fix each pedicle hook anchor to the fixation rod.

Existing pedicle hooks utilized within conventional spinal fixation systems can be problematic in that they are typically designed with relatively narrow blade portions that comprise a U-shaped hook. The blade portion of conventional pedicle hooks only contacts a small surface area of the bone surface to which they are engaged. Consequently, conventional pedicle hooks can often cut-through or otherwise damage bone surfaces. Additionally, conventional pedicle hooks can easily become dislodged from the bone structure against which they were engaged, resulting in potential further injury due to further bone and tissue damage.

SUMMARY OF THE INVENTION

The present invention includes a hook anchor for anchoring a fixation rod to a bone. The hook anchor includes a hook body shaped in a curve of diminishing radius and a locking mechanism. The locking mechanism is configured to securely fix the hook anchor to the fixation rod. The curve of diminishing radius may have a shape of at least a portion of a Fibonacci curve. The bone can include at least one of a rib, a pelvis, and a vertebra. The hook body can be configured to engage with at least one of a spinous process a transverse process, and a pedicle of the vertebra.

In some aspects, the techniques described herein relate to a hook anchor for anchoring a fixation rod to a bone, including: a hook body shaped in a curve, wherein at least a portion of the curve is a portion of a logarithmic spiral; and a locking mechanism coupled to the hook body, the locking mechanism being configured to securely fix the hook anchor to the fixation rod.

In some aspects, the techniques described herein relate to a hook anchor, wherein at least a portion of an interior surface of the hook body is concave so that a first side ridge is formed along a first edge of the interior surface of the hook body and a second side ridge is formed along a second edge of the interior surface of the hook body.

In some aspects, the techniques described herein relate to a hook anchor, wherein the interior surface of the hook body at a first end of the hook body includes a projection extending towards an interior of the hook body.

In some aspects, the techniques described herein relate to a hook anchor, wherein the locking mechanism is removably coupled to the hook body.

In some aspects, the techniques described herein relate to a hook anchor, wherein the locking mechanism is coupled to the hook body by a threaded connection.

In some aspects, the techniques described herein relate to a hook anchor, wherein the hook body includes a plurality of locking mechanism mount points and the locking mechanism is configured to be selectively coupled to each locking mechanism mount point of the plurality of locking mechanism mount points.

In some aspects, the techniques described herein relate to a hook anchor, wherein a length of the hook body is between 60 millimeters and 70 millimeters.

In some aspects, the techniques described herein relate to a hook anchor, wherein a width of the hook body is between 8 millimeters and 20 millimeters.

In some aspects, the techniques described herein relate to a hook anchor, wherein a thickness of the hook body is between 3 millimeters and 5 millimeters.

In some aspects, the techniques described herein relate to a hook anchor, wherein the hook body includes titanium, titanium alloy, stainless steel, ceramic, and/or a polymer.

In some aspects, the techniques described herein relate to a hook anchor, wherein the hook body is configured to engage a portion of bone that includes at least one of a rib, a pelvis, and a vertebra.

In some aspects, the techniques described herein relate to a hook anchor, wherein the hook body is configured to engage with at least one of a spinous process a transverse process, and a pedicle of the vertebra.

In some aspects, the techniques described herein relate to a hook anchor, including: a hook body shaped in a curve of diminishing radius, wherein the hook body is configured to engage a portion of bone that includes at least one of a spinous process a transverse process, and a pedicle of a vertebra; and a locking mechanism coupled to the hook body, the locking mechanism being configured to securely fix the hook anchor to a fixation rod.

In some aspects, the techniques described herein relate to a hook anchor, wherein at least a portion of an interior surface of the hook body is concave so that a first side ridge is formed along a first edge of the interior surface of the hook body and a second side ridge is formed along a second edge of the interior surface of the hook body.

In some aspects, the techniques described herein relate to a hook anchor, wherein the interior surface of the hook body at a first end of the hook body includes a projection extending towards an interior of the hook body.

In some aspects, the techniques described herein relate to a hook anchor, wherein the locking mechanism is removably coupled to the hook body.

In some aspects, the techniques described herein relate to a hook anchor, wherein: a length of the hook body is between 60 millimeters and 70 millimeters; a width of the hook body is between 8 millimeters and 20 millimeters; and a thickness of the hook body is between 3 millimeters and 5 millimeters.

In some aspects, the techniques described herein relate to a hook anchor, wherein the hook body includes titanium, titanium alloy, stainless steel, ceramic, and/or a polymer.

In some aspects, the techniques described herein relate to a spine stabilization system, including: a fixation rod; a first hook anchor, including: a first hook body shaped in a first curve, wherein at least a portion of the curve is a first portion of a first logarithmic spiral, and a first locking mechanism coupled to the first hook body, the first locking mechanism being configured to securely fix the first hook anchor to the fixation rod at a first location on the fixation rod; and a second hook anchor, including: a second hook body shaped in a second curve, wherein at least a portion of the second curve is a second portion of a second logarithmic spiral, and a second locking mechanism coupled to the second hook body, the second locking mechanism being configured to securely fix the second hook anchor to the fixation rod at a second location on the fixation rod.

In some aspects, the techniques described herein relate to a spine stabilization system, wherein: the first locking mechanism is removably coupled to the first hook body; and the second locking mechanism is removably coupled to the second hook body.

These and other features, aspects, and advantages of the present invention will become better understood upon consideration of the following detailed description, drawings and appended claims.

DETAILED DESCRIPTION OF THE INVENTION

Figure 1:
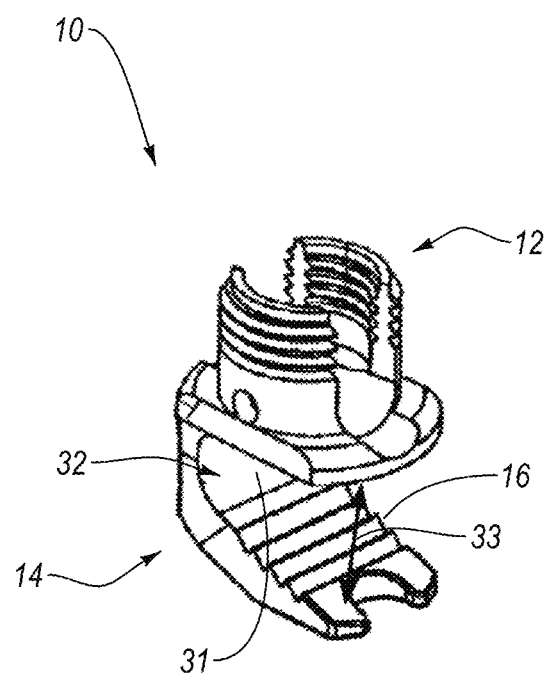
FIG. 1 is a perspective view depicting a conventional spinal fixation system pedicle hook.

The disclosure and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure the disclosure in detail. Skilled artisans should understand, however, that the detailed description and the specific examples, while disclosing preferred embodiments of the disclosure, are given by way of illustration only and not by way of limitation. Various substitutions, modifications, additions, or rearrangements within the scope of the underlying inventive concept(s) will become apparent to those skilled in the art after reading this disclosure.

It is to be understood that the invention may assume various alternative orientations, except where expressly specified to the contrary. It is also to be understood that the specific devices and processes illustrated in the attached drawings and described in the following specification are simply exemplary examples of the inventive concepts defined in the appended claims. Hence, specific dimensions and other physical characteristics relating to the examples disclosed herein are not to be considered as limiting, unless the claims expressly state otherwise.

As required, detailed examples of the present invention are disclosed herein. However, it is to be understood that the disclosed examples are merely exemplary of the invention that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present invention.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items can be employed. For example, if any assembly or composition is described as containing components A, B, and/or C, the assembly or composition can contain A alone; B alone; C alone; A and B in combination; A and C in combination; B and C in combination; or A, B, and C in combination.

A spinal stabilization system may be installed in a patient to stabilize or apply force to one or more vertebrae within the patient's spine to induce corrective movement or stabilization of those vertebrae. Spinal stabilization systems may be used in instances of abnormal spinal development or curvature due to diseases, injury or trauma, or genetic malformation. Improper curvature of the spine may lead to significant deformities, which can result in serious symptoms, such as pain, weakness, and, ultimately, pulmonary and cardia problems.

In conventional spinal fixation systems, pedicle hooks are used to engage pedicle bones of vertebrae of a spine. Spinal fixation systems typically include one or more hook anchors that are adapted to engage various surfaces of a patient's vertebrae. Such hooks are then coupled to a fixation element or rod that spans two or more vertebrae. A locking mechanism is effective to securely interconnect the hooks and the fixation rod.

FIG. 1 is a perspective view depicting a conventional spinal fixation system pedicle hook 10. Pedicle hook 10 includes body portion 12 and hook 14. Hook 14 generally has an open "C-shape" in which hook 14 has a generally consistent radius of curvature, in which the inner surface 31 of hook body 14 forms a U-shape or semi-circle. Consequently, the gape 33 of hook body 14 is the widest portion of the interior volume 32 of hook 14. This geometry allows pedicle hook 10 to be easily positioned over a bone structure. However, this simultaneously make it relatively easy for the bone structure to be dislodged out of hook 14 of pedicle hook 10.

Consequently, some conventional pedicle hooks 10 incorporate a serrated surface 16 in an attempt to improve grip and prevent the pedicle hook 10 from becoming dislodged after the spinal fixation system is surgically placed within a patient. The serration 16 is typically designed to prevent shifting of the hook 10 after implantation.

Unfortunately, this design, in which the width W of hook 14 is typically around 3 millimeters (mm), allows substantially movement of hook 14 with respect to the bone against which hook 14 is installed. The narrow width of hook 14 can result in excessive pressure being asserted against the bone structure in a small area, potentially resulting in bone fracturing, particularly in pediatric patients. Additionally, any serration or other surface treatments 16 applied to the inner surface of hook 14, in combination with that relative movement, can result in hook 14 acting as a sawing member to cut through or otherwise damage the bone structure against which hook 14 is positioned.

Body portion 12 allows for pedicle hook 10 to be securely fastened to such a fixation rod.

To remedy deficiencies with existing spine stabilization systems and to provide other benefits and improvements, the present disclosure provides a spinal hook that may operate as universal anchoring member of a spinal stabilization system. As described herein, the present hook anchor may be utilized as a transverse process, rib, spinous process, and pelvis (e.g., posterior iliac spine) universal hook. The present hook anchor is configured with a more favorable geometry as compared to conventional spinal hooks to mitigate or reduce problems or complications including bone breakage, fracturing, and sawing encountered when using conventional hooks as anchors for treatments. In conventional systems, these deficiencies may cause patients (and, particularly, pediatric patients) to require multiple additional surgeries because of anchor dislodgment issues and bone breakage.

In an embodiment, the present hook anchor is approximately shaped in the form of a portion of a Fibonacci curve. This configuration may be described as a hook in which the strip of material making up the hook is arranged into a curve (when viewed from the side) and when moving from an outer position on the hook to an inner position having continuously diminishing radius. As such, the present hook anchors may be considered a "closed" hook design in which an object cannot be positioned into an interior volume of the anchor hook via directly linear movement of the object towards an interior of the hook anchor (in contrast to conventional "U-shaped" or open hooks). As such, the present hook anchor is not simply placed over or against a vertebral or pelvic process. Instead, the present anchor hook is typically rotated onto the bone process as part of installation. As described herein, this configuration enables the present anchor hook to be more securely fastened to vertebral, rib, pelvic or other bone processes when utilized as part of a stabilization system.

In the present hook anchor, each tip of the flanges of the hook anchor may each include on their inner surfaces small projections that extend towards an interior volume of the hook anchor. The projections may take the form of a bump or detent that may further act to retain an engaged object (i.e., a bone process) within an interior volume of the hook anchor. Although the two flanges of the hook anchor may take various geometries as described herein, each flange may be tapered so as to have a width at each flange tip ranging from 3 millimeters (mm) to 5 mm. In other embodiments, however, the flange tips may have different sizes and shapes.

During use of the present hook anchor within a spine stabilization system, the bone structure to which the hook anchor is engaged is typically positioned in the bottom of the anchor shape, which is typically the widest portion of the interior volume of the hook anchor. By positioning a bone structure within the interior portion of the hook anchor, the hook anchor has a larger internal surface area for contact against the bone structure and provides more secure coupling between the hook anchor and the bone structure as compared to conventional hook devices.

Figure 2A:
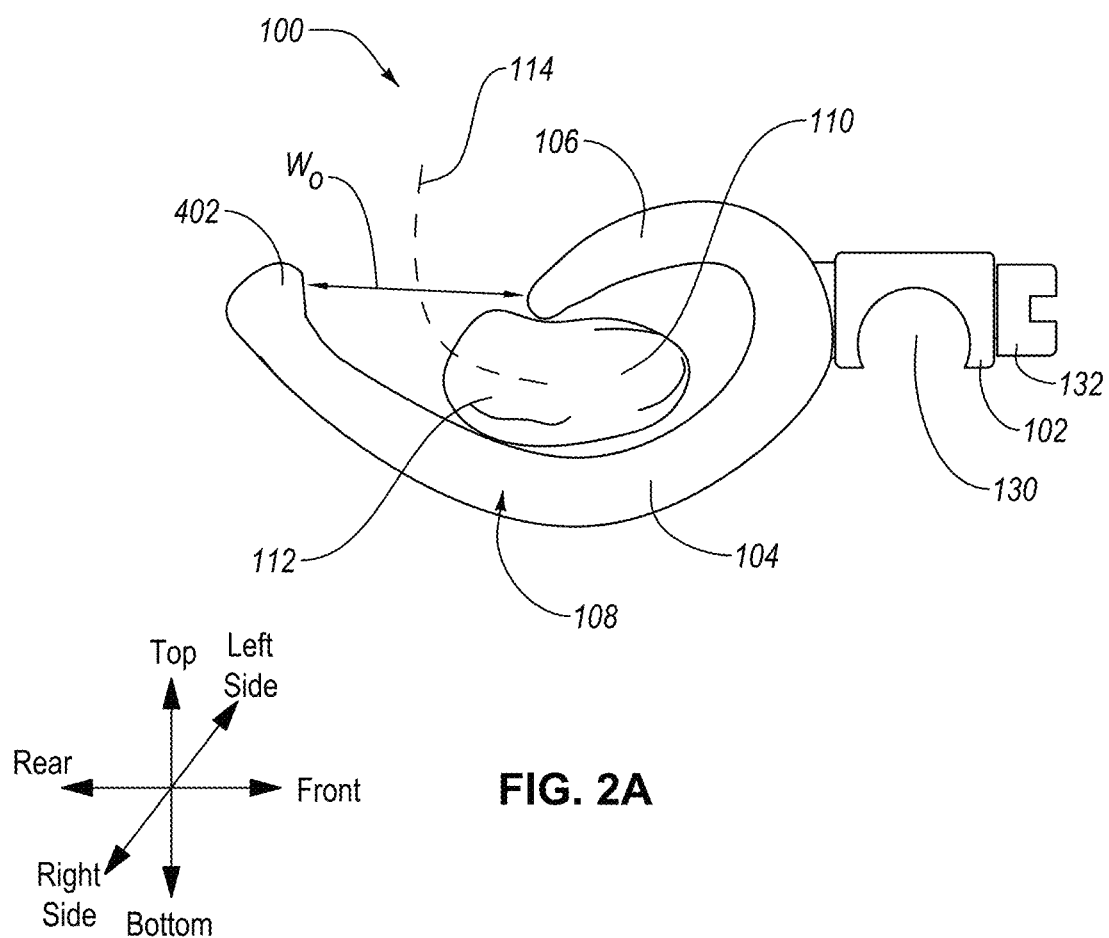
FIGS. 2A-2I shows various perspective views of a hook anchor in accordance with the present disclosure.
Figure 2B:
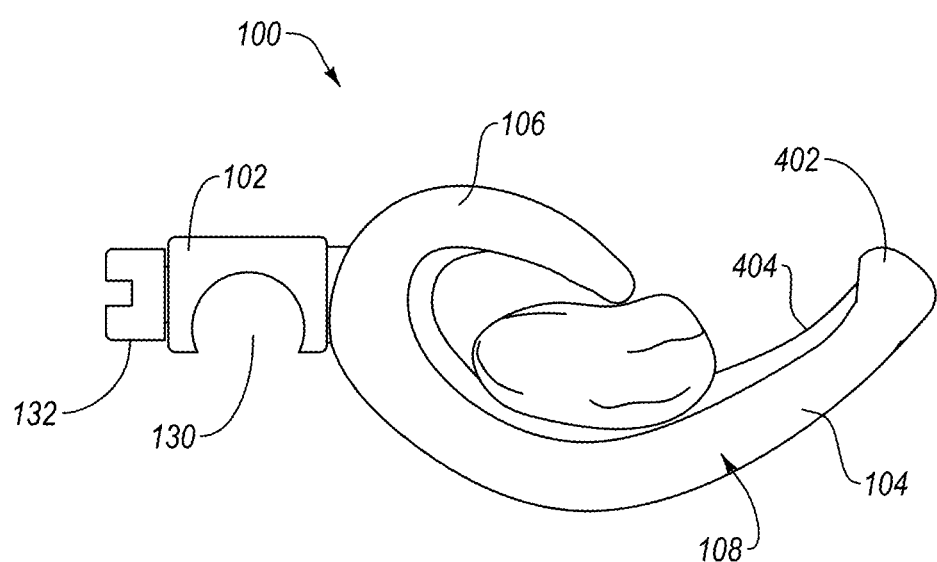
Figure 2C:
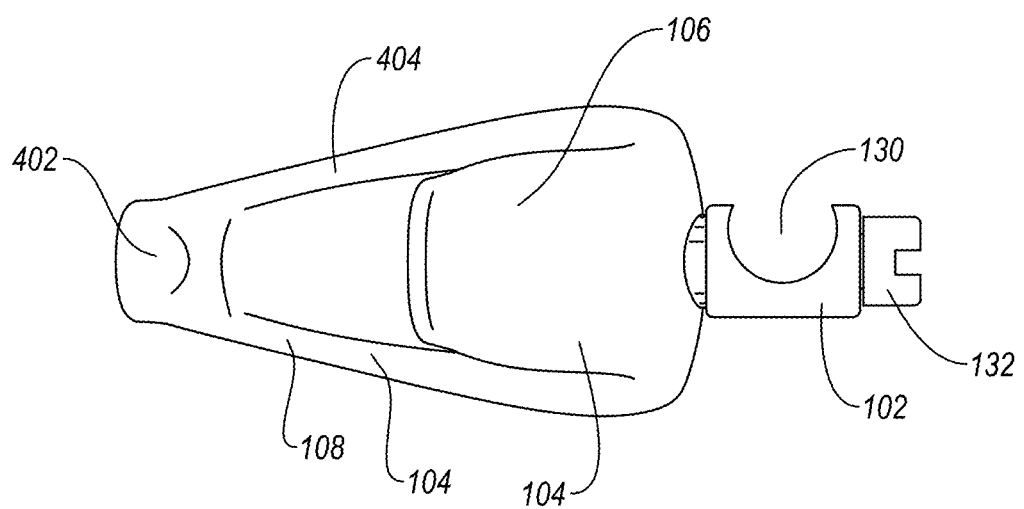
Figure 2D:
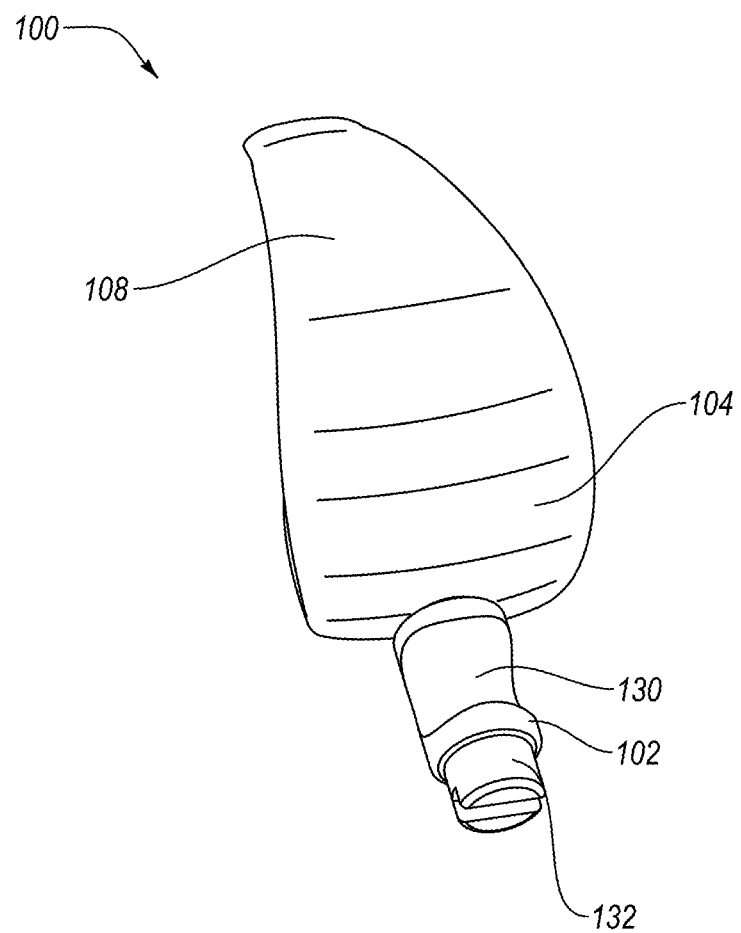
Figure 2E:
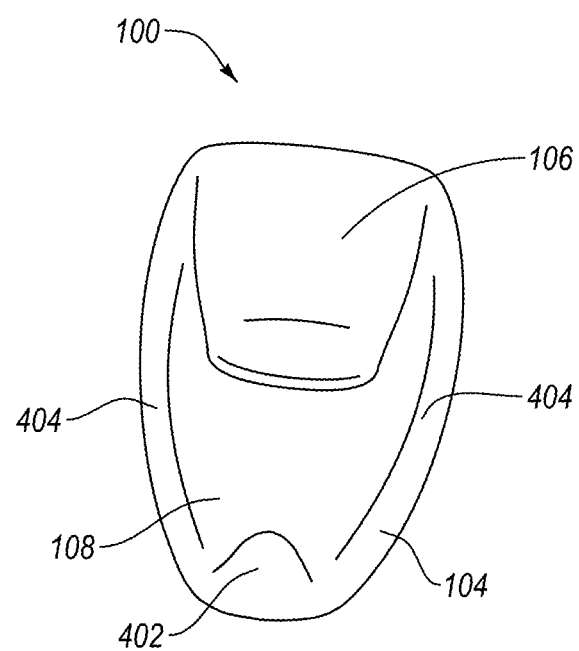
Figure 2F:
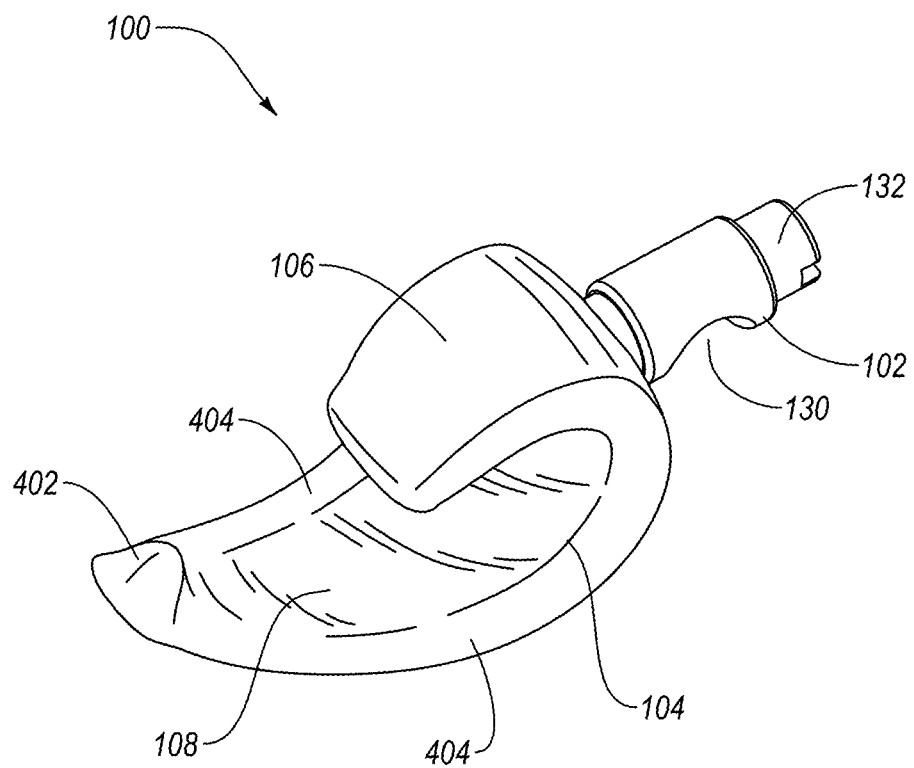
Figure 2G:
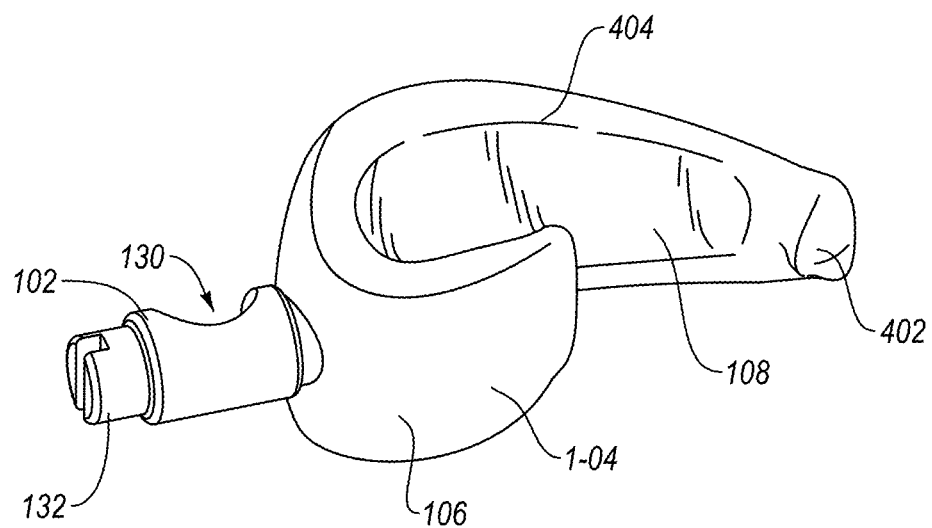
Figure 2H:
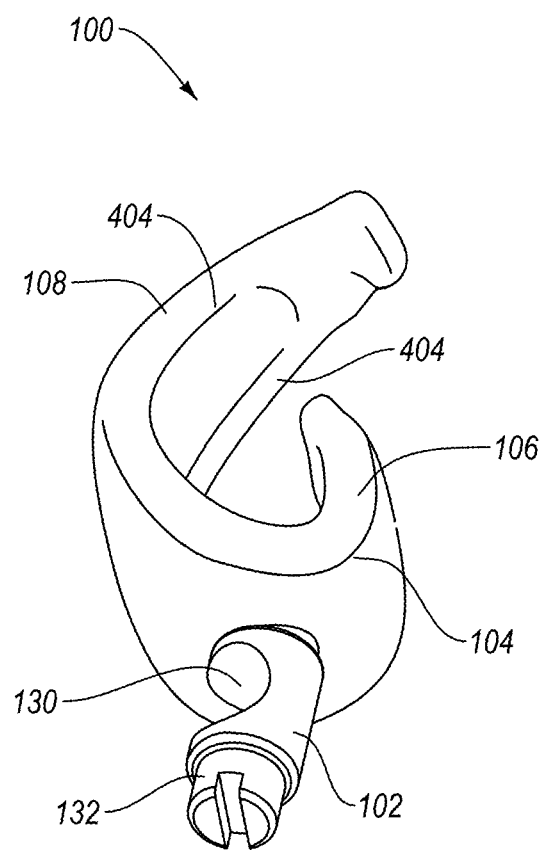
Figure 2I:
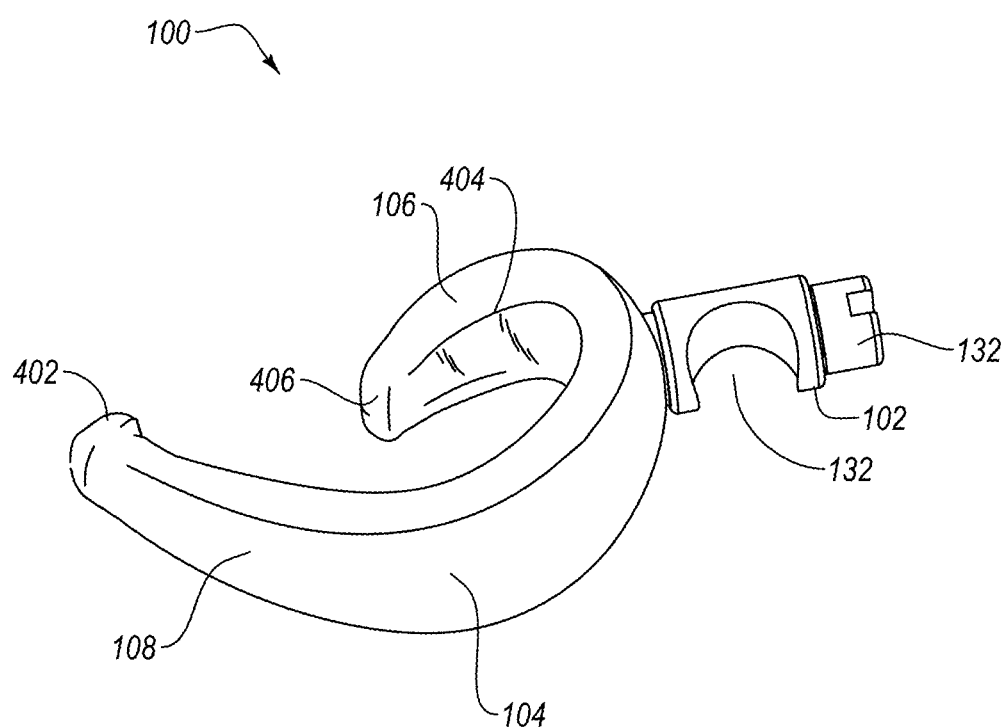

FIGS. 2A-2I shows various perspective views of a hook anchor 100 in accordance with the present disclosure. FIG. 2A shows a right-side view of hook anchor 100. FIG. 2B shows a left side view of hook anchor 100. FIG. 2C shows a top view of hook anchor 100. FIG. 2D shows a perspective back view of hook anchor 100. FIG. 2E shows a perspective rear view of hook anchor 100. FIG. 2F shows a perspective right side view of hook anchor 100. FIG. 2G shows a perspective top and right-side view of hook anchor 100. FIG. 2H shows a perspective front view of hook anchor 100. FIG. 2I shows a perspective bottom view of hook anchor 100. The terms describing the layout of hook anchor 100 are illustrated in FIG. 2A.

Hook anchor 100 includes locking mechanism 102 and hook body 104. Hook body 104 is connected to locking mechanism 102 at a fixed connection. In embodiments, hook body 104 and locking mechanism 102 may be of unitary construction or may represent two separate components of hook anchor 100 that are fixedly coupled together. By way of non-limiting example, hook body 104 can be welded, ultrasonically or chemically bonded, adhesively attached or mechanically mated to locking mechanism 102. In various embodiments one or both of hook body 104 and locking mechanism may include one or more of titanium, titanium alloys, stainless steel, ceramics, polymers and/or other suitable materials providing adequate strength and being suitable for implantable devices.

In various embodiments, locking mechanism 102 may be configured to be removable from hook body 104 (e.g., via a threaded or other locking connection) enabling locking mechanism 102 to be selectively fixed to hook body 104. In some embodiments, for example, locking mechanism 102 may include a threaded coupling enabling locking mechanism 102 to be screwed into a screw hole formed within hook body 104. In such an arrangement, hook body 104 may include a number of different screw hole formed in different locations within hook body 104 (e.g., along the outer surface or the edges of hook body 104) allowing a suitably configured locking member 102 to be affixed to hook body 104 in a number of different locations and configuration. In that case, two or more locking mechanisms 102 may be affixed to the hook body 104 at the different attachment points.

Hook body 104 has an upper portion 106 comprising a first flange and a lower portion 108 comprising a second flange. Upper and lower portions 106 and 108, can be integrally formed, or alternatively, they can comprise two separate elements that have been mated together using any of the mating techniques known in the art.

Hook body 104 is generally shaped to define an interior volume 110 of hook body 104. Interior volume 110 is sized to fit around a bone feature 112 (e.g., a bone process or pedicle, such as a vertebral transverse process, spinous process, or pedicle, a rib, or a pelvic feature), as is illustrated in FIG. 2A.

To enable hook body 104 to be positioned around bone feature 112, the respective tips of the flanges of upper portion 106 and lower portion 108 define an opening having a width Wo that is sized to allow hook body 104 to be positioned over bone feature 112. Depending on the material and construction of hook body 104, to enable positioning over bone feature 112, hook body 104 may be bent or otherwise temporarily reshaped to move the tip of upper portion 106 away from the tip of lower portion 108, thereby temporarily increasing the size of $W_O$. With hook body 104 being constructed of resilient material, after hook body 104 is installed around bone feature 112, hook body 14 may return to (or be biased towards) its original dimensions and shape thereby gripping or otherwise positively engaging with bone feature 112.

To install hook body 104 over bone feature 112, bone feature 112 is typically introduced into the interior volume 110 of hook body 104 by moving hook body 104 over bone feature 112 in a manner that causes bone feature 112 to follow path 114 through hook body 104. As such, installation of hook body 104 over bone feature 112 may require some degree of rotation of hook body 104, rather than hook body 104 simply being placed over bone feature 112. In this manner hook body 104 can be coupled to a bone feature 112 in a manner that does not allow the hook body 104 to become dislodged from bone feature 112 without bone feature 112 following path 114 in reverse (or hook body 104 moving in a manner that caused bone feature 112 to follow path 114 in reverse). In this manner, hook body 104 is securely engaged to bone feature 112 in a way that reduces the likelihood that hook body 104 becomes dislodged from bone feature 112.

Depending upon the geometrical attributes of the bone feature 112 to which hook body 104 is to be attached, the overall dimensions of hook body 104 may be adjusted. As such, the overall size of hook body 104 may be scaled-up to allow engagement with larger bone processes, while the overall size of hook body 104 may be scaled-down to allow engagement with smaller bone processes.

Locking mechanism 102, which is attached to hook body 104 is configured to fixedly engage with a fixation rod of a spine stabilization system thereby coupling the spine stabilization system to the bone feature 112 around which body 104 is engaged. Locking mechanism 102 includes recess 130, which is sized to fit around a fixation rod. With a fixation rod positioned within recess 130, lock 132 is configured to secure the fixation rod in place within recess 130.

Although an example locking mechanism 102 is depicted in the figures of the present application, it should be understood that hook body 104 may be utilized in conjunction with any type of locking or fixing mechanism that may be configured to securely attach hook body 104 to a fixation rod or other element of a spinal fixation system. For example, although locking member 102 is depicted as being a solid component that does not enable any portion of locking member 102 to move with respect to hook body, in various embodiments, locking member 102 may instead be coupled to hook body 104 through various types of hinges or flexible couplings. For example, locking mechanism 102 may be coupled to hook body 104 through a hinge mechanism or ball-and-socket connection enabling rotation or movement of locking mechanism 102 with respect to hook body 104.

Similarly, different types of lock 132 may be utilized in conjunction with locking mechanism 102 and hook body 104. Lock 132 may include one or more threaded portions enabling locking members to be introduced to and secured to locking mechanisms 102 to secure a fixation rod within recess 130. Other types of locks 102 may be utilized, such as chemical, magnetic, friction, and the like. In some embodiments, locking mechanisms 102 may include a hole or opening enabling a fixation rod to be introduced through a body of locking mechanism 102 and retained therein. Locking mechanism 102 is sized and shaped to engage properly with a fixation rod or other component or a spine stabilization system. In embodiments, locking mechanisms 102 has a length between about 3 and 50 millimeters (mm).

Although FIGS. 2A-2I depict locking mechanism 102 as being coupled to the outer surface of the front portion of hook body 104, it should be understood that in various implementations of hook anchor 100, anchor 100 may be manufactured so that locking mechanism 102 or formed upon or coupled to any surface of hook body 104.

Figure 3:
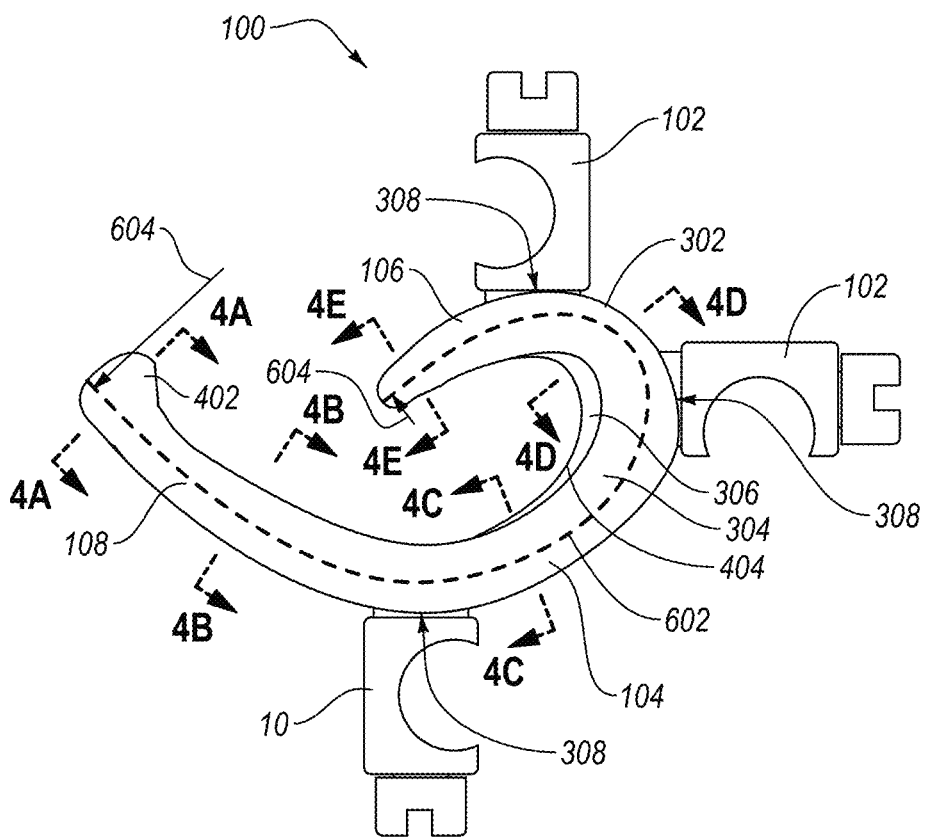
FIG. 3 depicts a hook anchor showing a number of potential placements of locking mechanisms upon an outer surface of the hook anchor.

For example, FIG. 3 depicts hook anchor 100 showing a number of potential placements of locking mechanism 102 upon outer surface 302 of anchor 100 including top, front, and bottom placements. In addition to being placed on outer surface 302 of hook body 104, locking mechanisms 102 may alternately (or in addition) be placed upon the side surfaces 304 (left and right sides) of hook body 104.

Any particular hook anchor 100 may include a single locking mechanism 102 positioned on one of the outer surface 302 or side surfaces 304 of hook body 104. Alternatively, two or more different locking mechanisms 102 (where each locking mechanism 102 may have the same or different construction) may be positioned on one or more of outer surface 302 and the side surfaces 304 of hook body 104.

In various embodiments, locking mechanisms 102 may be removable from hook body 104. For example, hook body 104 may include a number of mount points 308 to which locking mechanisms 102 may be attached. The mount points 308 may be distributed about the exterior surface of hook body 104 or the side surfaces of hook body 104, for example, allowing a locking mechanism 102 to be attached to hook body 104 in a variety of locations, potentially facilitating installation of hook anchor 100. In an embodiment, mounts points 308 comprises threaded holes to which an appropriately threaded portion of locking mechanism 102 may be removably coupled.

In various embodiments of hook anchor 100, the inner surface 306 (also referred to herein as the interior surface) of hook body 104 may have a cross-sectional contour configured to assist in securely engaging hook body 104 to a bone process (e.g., bone feature 112). To illustrate this specific contouring, FIGS. 4A-4E are cross-sectional views of hook body 104 taken along lines, 4A-4A, 4B-4B, 4C-4C, 4D-4D, and 4E-4E, respectively of FIG. 3.

Figure 4A:
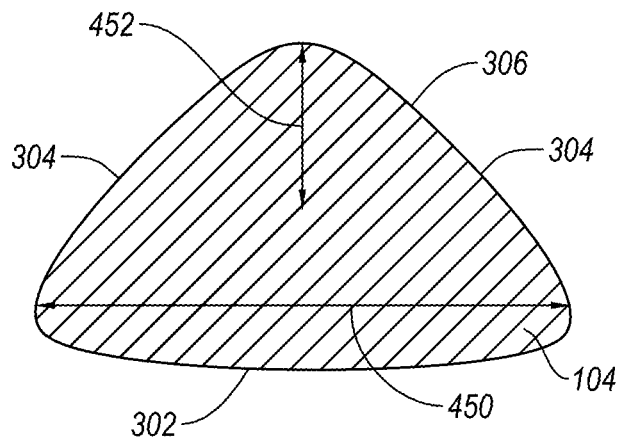
FIGS. 4A-4E are cross-sectional views of a hook body taken along lines, 4A-4A, 4B-4B, 4C-4C, 4D-4D, and 4E-4E, respectively of FIG. 3.

As illustrated in FIG. 4A, the inner surface 306 of hook body 104, at the tip of lower portion 108, includes a projection (e.g., projection 402 of FIGS. 2A-2I and 3) that extends away from inner surface 306 at the tip of lower portion 108 by a height 452. The projection may extend along a portion of the inner surface 306 of lower portion 108 away from the tip of lower portion 108 and operates as a barb or catch to prevent a bone process from passing over the projection. As such, projection 402 can assist in preventing hook body 104 from becoming accidentally dislodged from a bone process. In various embodiments, Projection 402 may only extend along inner surface 306 a distance ranging from 1 mm to 5 mm from the tip of lower portion 108. The height of projection 402 may range from 1 mm to 5 mm, depending upon the application.

Figure 4B:
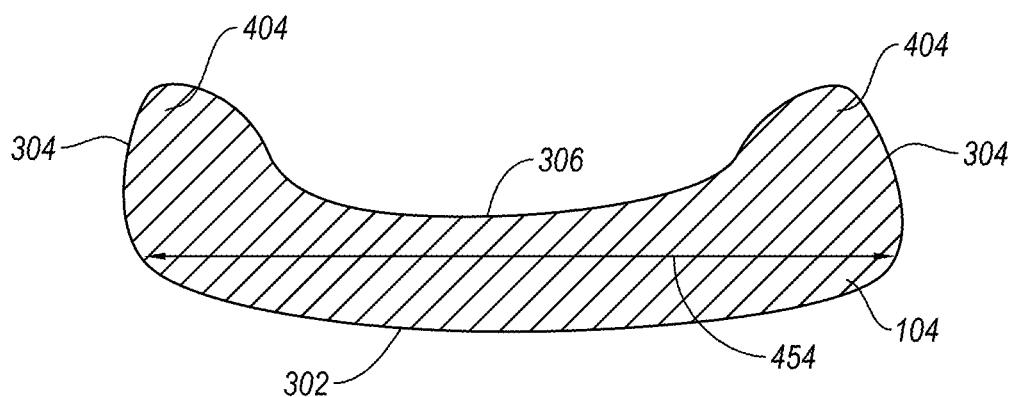
Figure 4C:
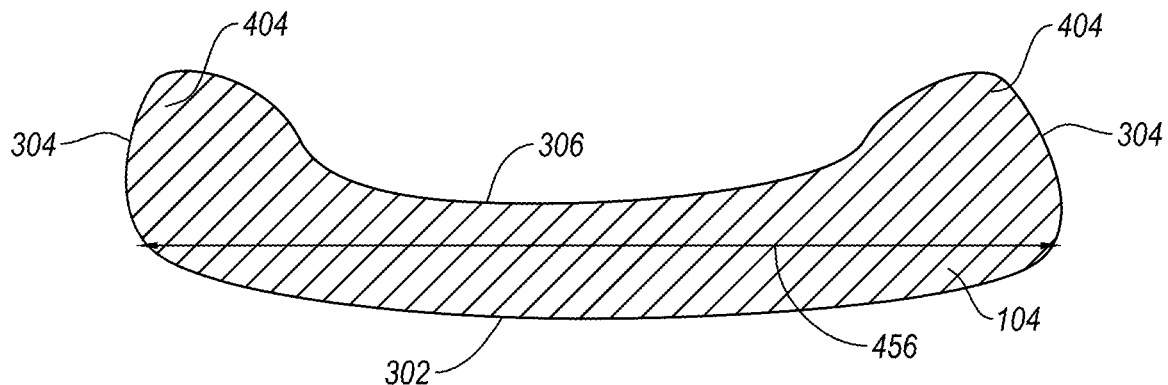
Figure 4D:
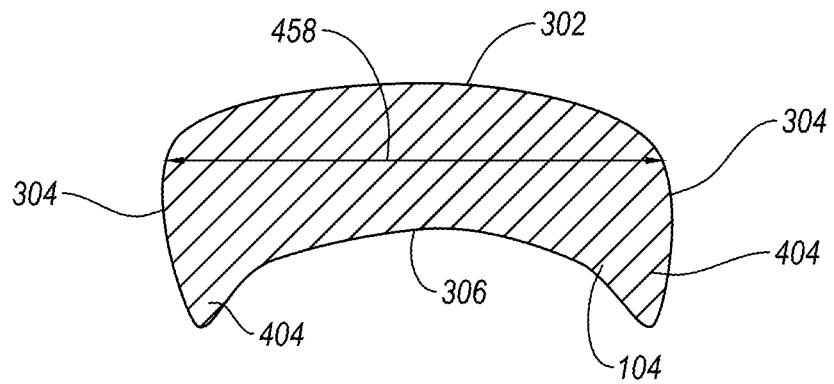

As illustrated in FIGS. 4B, 4C, and 4D moving along lower portion 108 of hook body from left to right and counterclockwise (as viewed in FIG. 3) and into upper portion 106, inner surface 306 of hook body 104 may, in embodiments, be concave to some degree to form side ridges 404 on either side of inner surface 306. When hook body 104 is engaged to a bone process, side ridges 404 may, at least along some length of side ridges 404, contact the bone surface and, given the small surface area of side ridges 404, may operate to more securely engage to the bone surface to provide a more secure engagement between hook body 104 and the bone process.

Figure 4E:
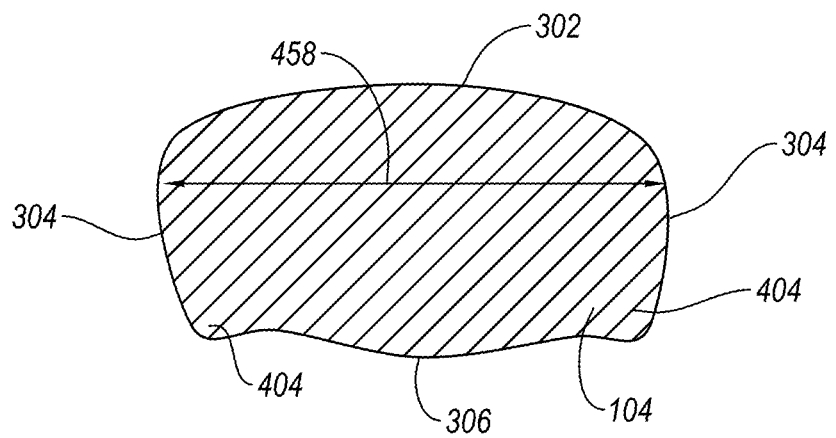

As illustrated in FIG. 4E, the inner surface 306 of hook body 104, at the tip of upper portion 106 is not concave and is instead relatively flat or continuously curved from edge 404 to edge 404 of hook body 104. Accordingly, the non-concave portion of inner surface 306 at the tip of upper portion 106 operates as a second projection 406 extending above the concave surface of inner surface 306 at location away from the tip of upper portion 106 (e.g., as illustrated in FIG. 4D). Accordingly, the non-concave portion of inner surface 306 illustrated in FIG. 4E operates as a barb or catch to prevent a bone process from passing over the top of upper portion 106 to assist in preventing hook body 104 from becoming accidentally dislodged from a bone process.

Figure 5:
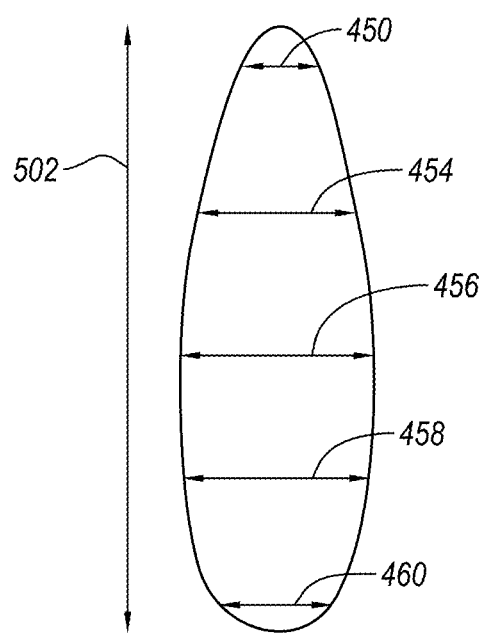
FIG. 5 depicts a hook body of a hook anchor if the hook body were to be unrolled out of the curved configuration shown in FIG. 3.

FIG. 5 depicts hook body 104 of hook anchor 100 if hook body 104 were to be unrolled out of the curved configuration shown in FIG. 3.

In embodiments, width 450 of the portion of hook body 104 depicted in FIG. 4A and FIG. 5 (e.g., the tip of lower portion 108) may have a thickness that ranges from 3 mm to 5 mm, though in other embodiments, width 450 may be adjusted for particular applications.

The height 452 of projection 402 may range from 2 mm to 3 mm, though in other embodiments, height 425 may be adjusted for particular applications.

In embodiments, width 454 of the portion of hook body 104 depicted in FIG. 4B and FIG. 5 may have a thickness that ranges from 8 mm to 15 mm, though in other embodiments, width 454 may be adjusted for particular applications.

In embodiments, width 456 of the portion of hook body 104 depicted in FIG. 4C and FIG. 5 may have a thickness that ranges from 10 mm to 20 mm, though in other embodiments, width 456 may be adjusted for particular applications.

In embodiments, width 458 of the portion of hook body 104 depicted in FIG. 4D and FIG. 5 may have a thickness that ranges from 10 mm to 15 mm, though in other embodiments, width 458 may be adjusted for particular applications.

In embodiments, width 460 of the portion of hook body 104 depicted in FIG. 4E and FIG. 5 may have a thickness that ranges from 10 mm to 15 mm, though in other embodiments, width 458 may be adjusted for particular applications.

In its "unrolled" configuration, hook body 104 may have a length 502 (see FIG. 5) that ranges from 60 mm-70 mm, though in other embodiments, length 502 may be adjusted for particular applications.

Hook body 104 may have a thickness that ranges from 1 mm to about 3 mm, though in different applications and using different materials, hook body 104 may have different thicknesses.

Figure 6:
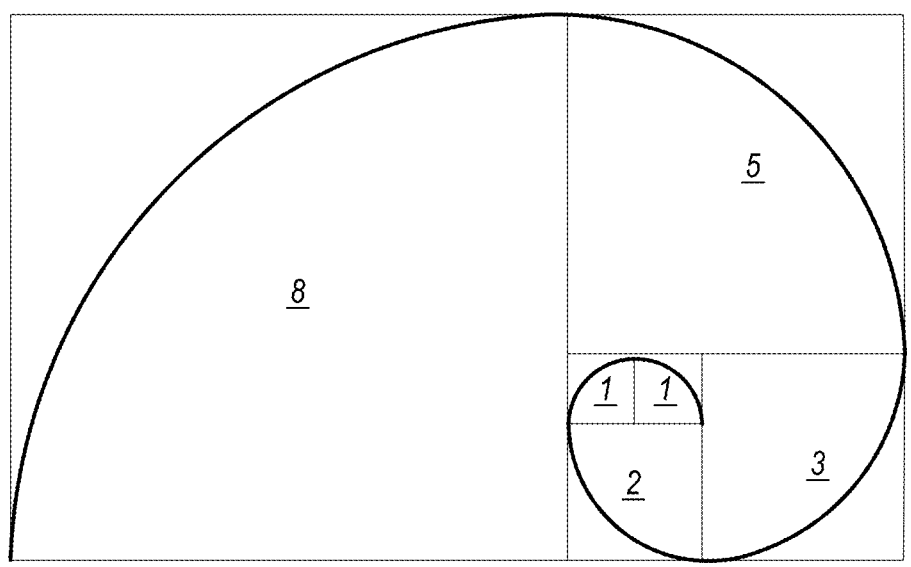
FIG. 6 depicts a Fibonacci curve.

As illustrated in FIG. 3, the shape of hook body 104 generally follows a curve 602. Curve 602 of hook body 104 may be generally described as a portion of a Fibonacci curve (as illustrated in FIG. 6). In general, curve 602 is shaped with diminishing radius of curvature moving from the tip of lower portion 108 along the curve 602 towards the tip of upper portion 106 in a counterclockwise direction (as viewed in FIG. 3). Additionally, curve 602 is closed so that the vector 604 defining the radius of curvature of curve 602 rotates from its orientation at the tip of lower portion 108 to its orientation at the tip of upper portion 106 anticlockwise (as viewed in FIG. 3) by about 270 degrees so that if upper portion 106 were to be extended, upper portion 106 would contact lower portion 108.

A logarithmic spiral is a spiral with a growth factor of φ, which is the golden ratio (i.e., a value of approximately 1.618). Logarithmic spirals are self-similar in that the spiral has the same or approximately the same shape are sub-parts of the spiral. That is, the entire spiral has the same shape as a smaller section of itself. In Cartesian coordinates, a logarithmic spiral can be presented parametrically by the following equations:

$$x = \alpha \cos \theta e^{b\theta} \qquad \text{Equation (1)}$$

$$y = \alpha \sin \theta e^{b\theta} \qquad \text{Equation (2)}$$

In Equations 1 and 2, the values a and b are constants that establish the geometry of a particular spiral. The Fibonacci spiral approximates a logarithmic spiral and may be approximated as a spiral that get wider or further from its origin point by a factor of φ for every quarter turn the spiral makes.

As described herein, the shape of the present hook body 104 may be derived from (or at least partially derived from) the Fibonacci spiral or other logarithmic curves that grow with a particular growth factor. Such curves or spirals, when viewed by moving along the curve or spiral from an outside point on the curve or spiral towards an inside point on the curve or spiral may also be viewed as curves or spirals of diminishing radius.

Figure 7:
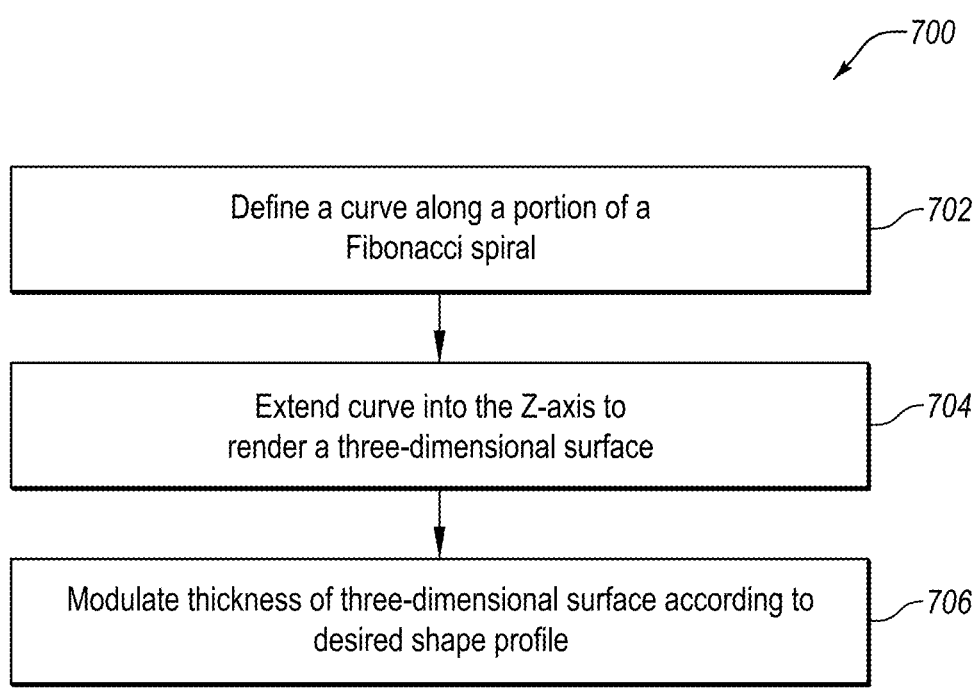
FIG. 7 is flow chart depicting a method of constructing a hook body in accordance with the present disclosure and wherein a geometry of the hook body is determined by the Fibonacci spiral.

As described herein, such curves may be utilized to construct or to at least design the curvature of the hook body 104 in accordance with the present disclosure. As a specific example, FIG. 7 is flow chart depicting a method of constructing a hook body 104 in accordance with the present disclosure and wherein a geometry of hook body 104 is determined by the Fibonacci spiral.

Figure 8A:
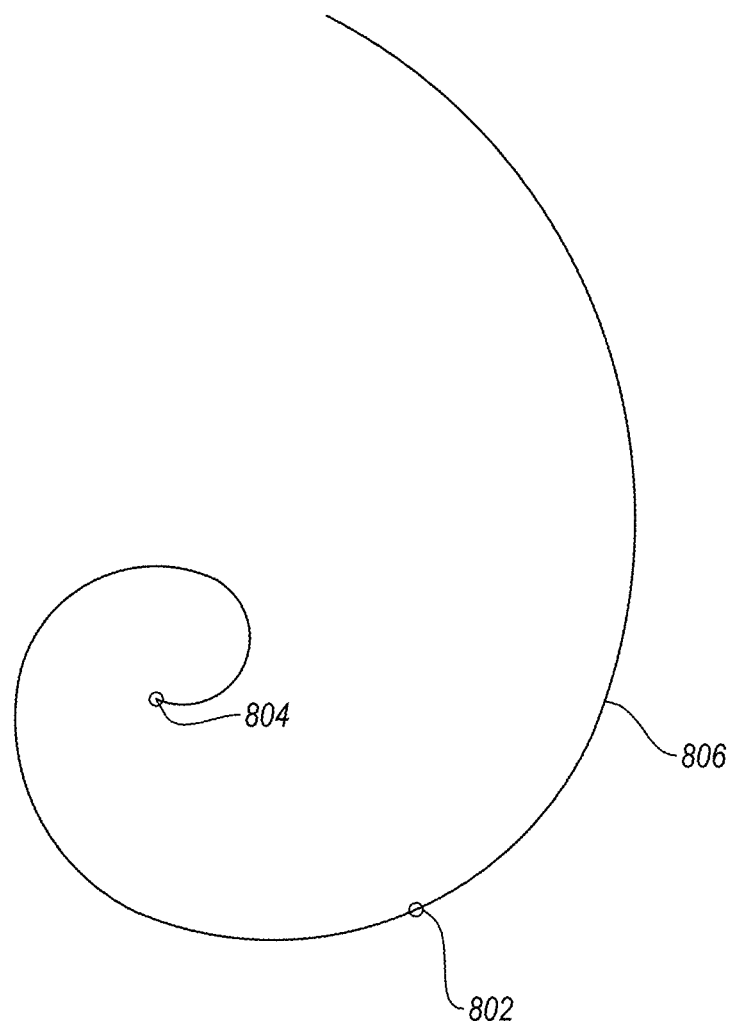
FIG. 8A depicts a sample Fibonacci spiral as rendered in an x-y plane, where the curve has been rotated 135 degrees counterclockwise from its conventional presentation.
Figure 8B:
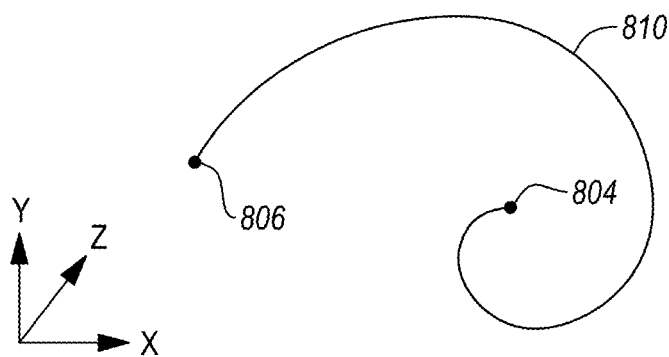
FIG. 8B depicts a Fibonacci curve defined along a length of a Fibonacci spiral by an origin point and an end point.

In a first step 702, a first Fibonacci curve is defined as a portion of a Fibonacci spiral. To illustrate, FIG. 8A depicts a sample Fibonacci spiral 802 as rendered in an x-y plane, where the curve has been rotated 135 degrees counterclockwise from its conventional presentation. Fibonacci spiral 802 includes an origin point 804 at the center of Fibonacci spiral 802. A Fibonacci curve 810 is defined along the Fibonacci spiral 802 that extends from the origin point 804 to an end point 806. The length of the curve along Fibonacci spiral 802 from origin point 804 to end point 806 can ultimately defines the length of hook body 104 (e.g., the dimension 502 as illustrated in FIG. 5). FIG. 8B depicts the Fibonacci curve 810 of Fibonacci spiral 802 as defined by origin point 804 and end point 806.

After the Fibonacci curve 810 has been defined, in step 704 of method 700 the Fibonacci curve 810 is extended along the z-axis to form a 3-dimensional surface 812 that traces along the length of the Fibonacci curve 810. Specifically, Fibonacci curve 810 is extended in the z-axis direction by a distance 814, which will ultimately determine the width of the hook body 104 manufactured in accordance with method 700.

In step 706 of method 700, with the 3-dimensional surface created in step 702, the thickness of the 3-dimensional surface 812 is modified to create the final design of the hook body 104.

Specifically, the thickness of surface 812 is modified according to a shape profile the designates a particular shape contour for each region of surface 812. For example, the shape profile may specify particular thicknesses for various points along the length of surface 812 and across the width of surface 812. In an embodiment, the shape profile may specify that the thickness of surface 812 be adjusted to correspond to a hook body 104 having the same cross-sectional shapes as those illustrated in FIGS. 4A-4E. In still other embodiments, the shape profile may further specify a desired width of hook body 104 so that the resulting hook body hook body 104 has the same width as the shape depicted in FIG. 5 and described above.

Figure 8C:
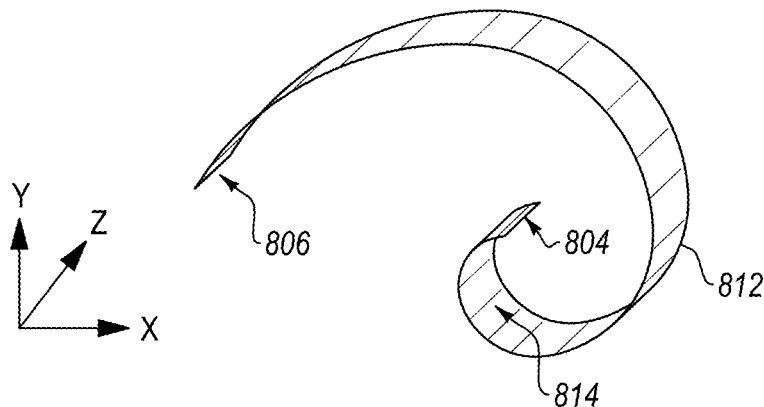
FIG. 8C depicts a Fibonacci curve rendered as a surface in a 3D space.
Figure 8D:
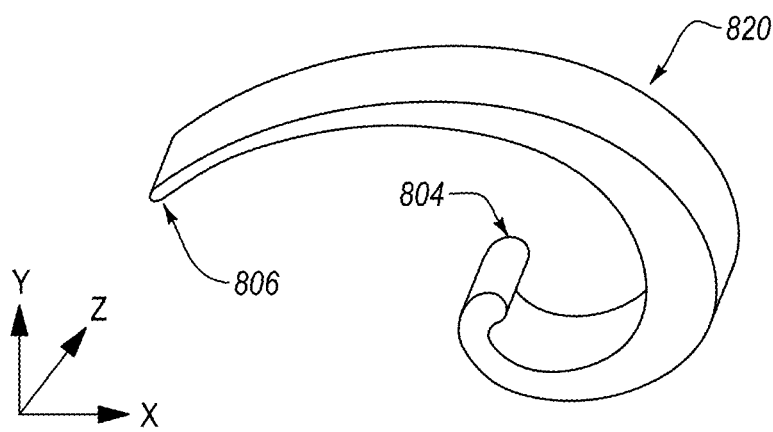
FIG. 8D depicts a 3D anchor body.

In this manner, after applying the shape profile as described above, the 3-dimensional surface 812 of FIG. 8C can be translated into the 3-dimensional object 820 as illustrated in FIG. 8D. A hook body 104 may then be manufactured in accordance with the 3-dimensional object 820 (e.g., via 3d printing, casting, or any other suitable manufacturing technique) to manufacture a hook body 104 having the same shape as 3-dimensional object 820. During this process, any suitable combination of locking mechanism 102 or other fixing member may be attached to hook body 104 or incorporated therein.

Hook anchor 100 is adapted for use in a spinal fixation system. By way of non-limiting example, a spinal fixation system according to the present invention can include two of more hook anchors 100, a fixation rod, and a locking mechanism configured to attach each hook anchor to the fixation rod. Specifically, locking mechanism 102 of hook anchor 100 is configured to receive the fixation rod, while the hook body 104 of the hook anchor 100 is adapted to engage a bone process, such as a vertebral transverse process or spinous process, a rib, pelvis. Locking mechanism 102 is effective to tightly secure the fixation rod to hook anchor 100. In use, a number of hook anchors 100 (in combination with other anchoring hardware) are first placed loosely on the target bone processes. The fixation road is then seated and placed within the locking mechanisms 102 of the hook anchors 100, the locking mechanisms 102 are tightened to securely interconnect the fixation rod and the hook anchors 100.

Figure 9A:
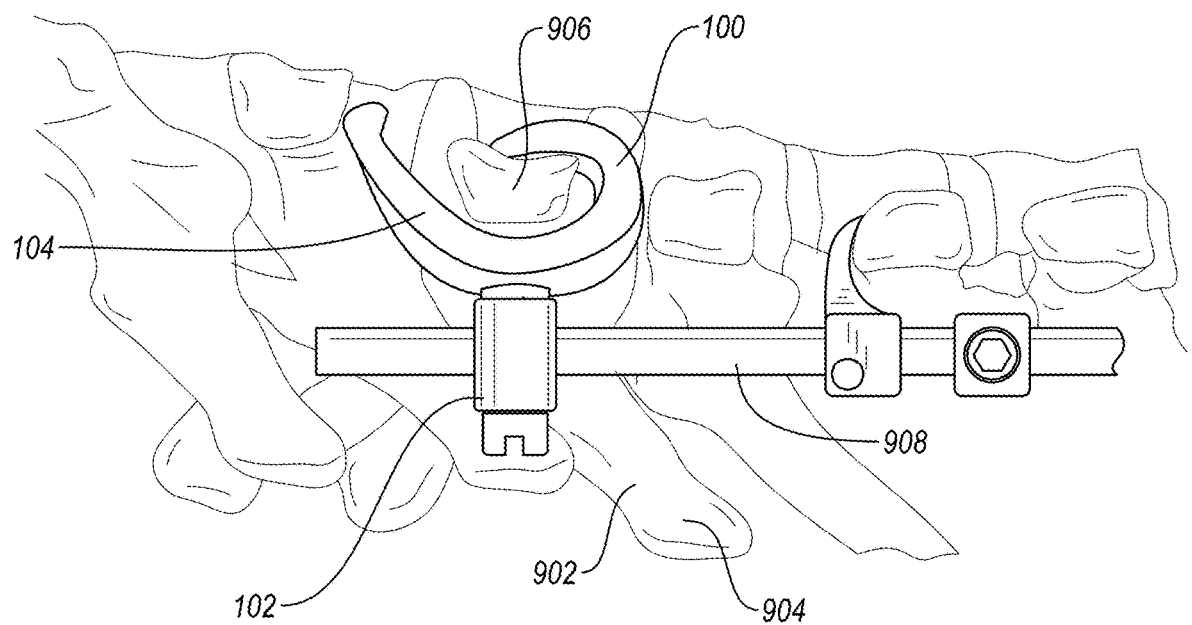
FIGS. 9A-9B depict perspective views of one embodiment of a spinal stabilization system on a vertebra forming a portion of the spine.
Figure 9B:
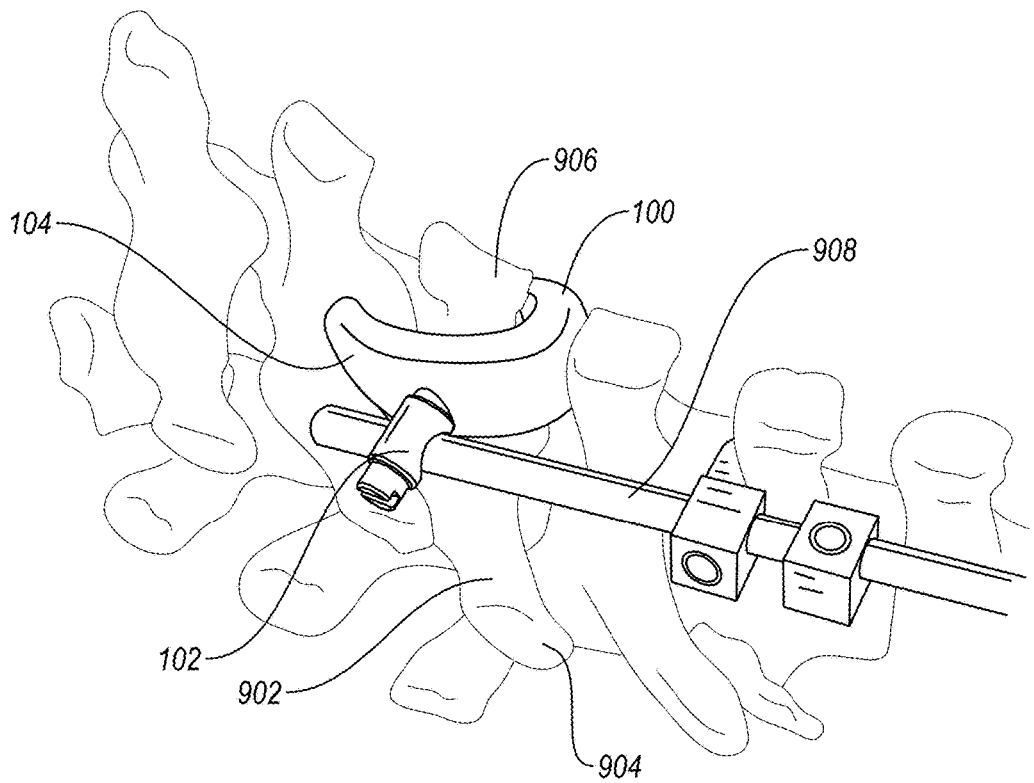

To illustrate, FIGS. 9A-9B depict perspective views of one embodiment of a spinal stabilization system on a vertebra 902 forming a portion of the spine. FIG. 9A shows a right-side view of the spine, FIG. 9B shows a perspective rear and right side of the spine. Those skilled in the art will appreciate that FIGS. 9A-9B are presented for simplicity purposes and in embodiments different numbers of hook anchors 100 may be attached to combinations of adjacent and non-adjacent vertebrae or other bone structures, including portions of the pelvis and ribs. Each vertebra may include spinous process 904 projecting from posterior wall and two transverse processes 906 projecting from sides of vertebra 902.

Hook anchor 100 of the present disclosure is adapted for use in a spinal fixation system. By way of non-limiting example, a spinal fixation system according to the present invention can include hook anchor 100 (comprising hook body 104 and locking mechanism 102) and fixation rod 908.

Locking mechanism 102 is effective to receive fixation rod 908, while the hook body 104 of hook anchor 100 is adapted to engage bone process 906. Locking mechanism 102 is effective to tightly engage with fixation rod 908. In use, hook anchor 100 is first placed loosely on the target bone process 906. Locking mechanism 102 is then tightened to securely couple fixation rod 908 to hook anchor 100, as illustrated in FIGS. 9A-9B.

Figure 10A:
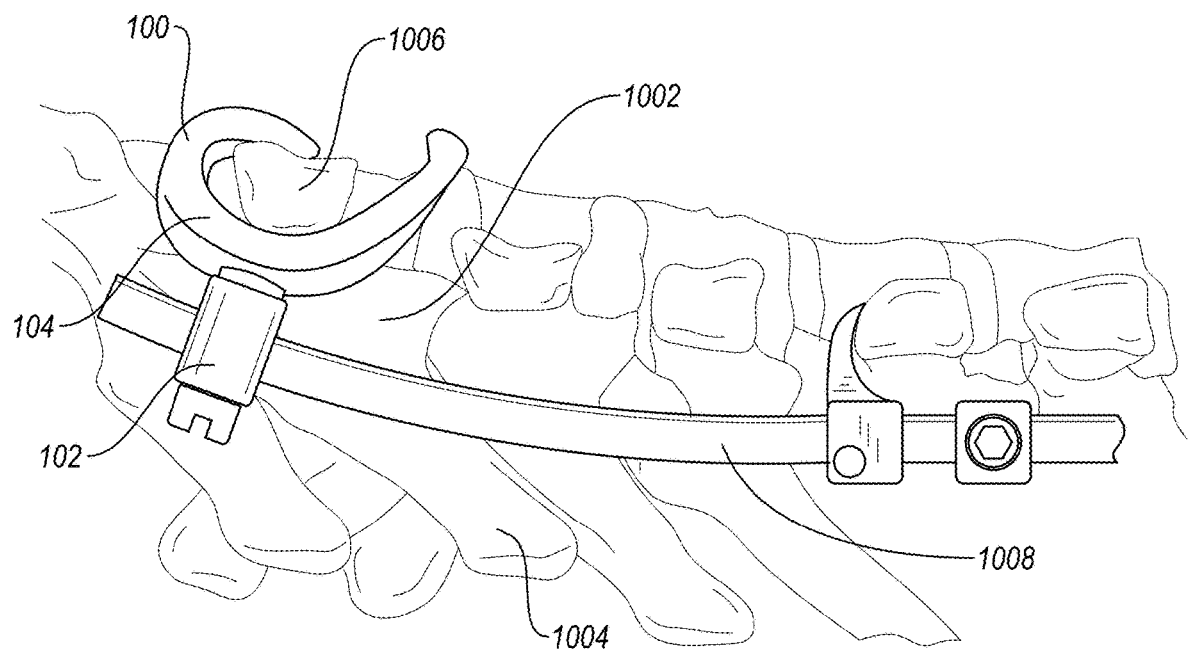
FIGS. 10A-10B depict perspective views of another embodiment of a spinal stabilization system on a vertebra forming a portion of the spine.
Figure 10B:
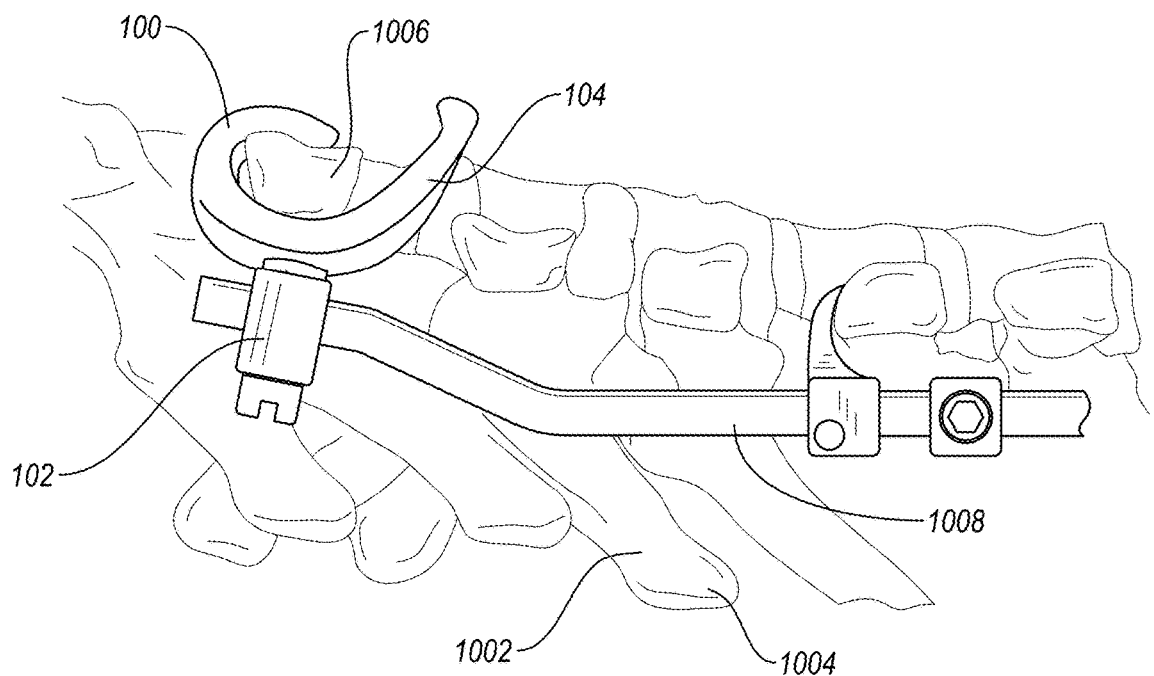

FIGS. 10A-10B depict perspective views of one embodiment of a spinal stabilization system on a vertebra 1002 forming a portion of the spine. FIG. 10A shows a right-side view of the spine and FIG. 10B shows a perspective right side view of the spine. Those skilled in the art will appreciate that FIGS. 10A-10B are presented for simplicity purposes and in embodiments different numbers of hook anchors 100 may be attached to combinations of adjacent and non-adjacent vertebrae or other bone structures, including portions of the pelvis and ribs. Each vertebra may include spinous process 1004 projecting from posterior wall and two transverse processes 1006 projecting from sides of vertebra 1002.

Hook anchor 100 of the present disclosure is adapted for use in a spinal fixation system. By way of non-limiting example, a spinal fixation system according to the present invention can include hook anchor 100 (comprising hook body 104 and locking mechanism 102) and fixation rod 1008. Locking mechanism 102 is effective to receive fixation rod 1008, while the hook body 104 of hook anchor 100 is adapted to engage bone process 1006. Locking mechanism 102 is effective to tightly engage with fixation rod 1008. In use, hook anchor 100 is first placed loosely on the target bone process 1006. Locking mechanism 102 is then tightened to securely couple fixation rod 1008 to hook anchor 100, as illustrated in FIGS. 10A-10B.

Figure 11:
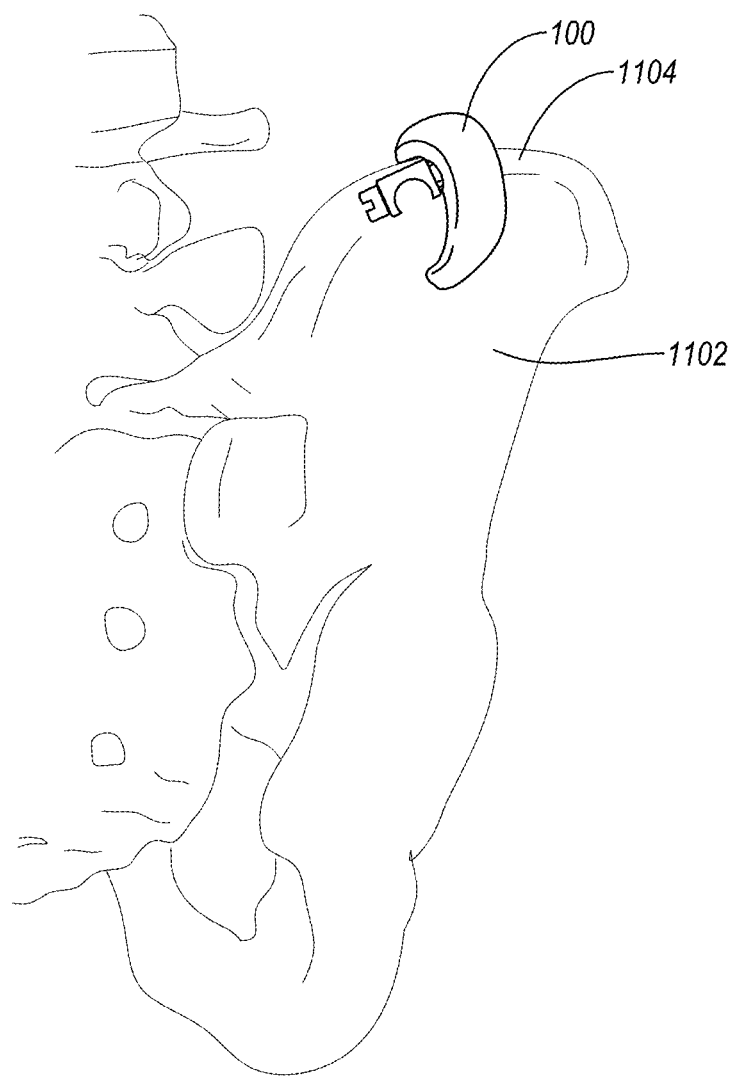
FIG. 11 shows a hook anchor mounted along a portion of an iliac crest of a pelvis.

FIGS. 9A-9B and 10A-10B depict various uses of hook anchor 100 in which hook anchor 100 is mounted vertebral processes. However, hook anchor 100 may be mounted to any suitable bone process. FIG. 11, for example, shows hook anchor 100 mounted along a portion of the iliac crest 1104 of pelvis 1102.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials.

Some embodiments of stabilization systems disclosed herein may provide greater freedom of movement to facilitate the healing process. In some embodiments, dynamic stabilization systems allow for motion such as twisting, lateral bending, torsion, flexion, and extension. In some embodiments, a dynamic stabilization system may be coupled to one or more spinous processes, transverse processes, and/or pedicles.

It will be understood by one having ordinary skill in the art that construction of the described invention and other components is not limited to any specific material. Other exemplary examples of the invention disclosed herein may be formed from a wide variety of biologically compatible materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate support members being integrally formed as a single unitary body with one another or with the two components. Such joining may be permanent in nature or may be removable or releasable in nature unless otherwise stated.

Furthermore, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably couplable" to each other to achieve the desired functionality. Some examples of operably couplable include, but are not limited to, physically mateable, physically interacting components, wirelessly interactable, wirelessly interacting components, logically interacting, and/or logically interactable components.

It is also important to note that the construction and arrangement of the elements of the invention as shown in the examples are illustrative only. Although only a few examples of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or support members or connectors or other elements of the system may be varied, the nature or number of adjustment positions provided between the elements may be varied. It should be noted that the elements and/or assemblies of the system might be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary examples without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting. In addition, variations and modifications can be made on the aforementioned structures and methods without departing from the concepts of the present invention and such concepts are intended to be covered by the following claims unless these claims by their language expressly state otherwise.

What is claimed is:

1. A hook anchor for anchoring a fixation rod to a bone, comprising:
   a hook body shaped in a curve, wherein the curve is a closed logarithmic spiral and a first rotation vector defining a radius of curvature at a first end of the curve is rotated by at least 270 degrees from a second rotation vector defining a second radius of curvature at a second end of the curve; and a locking mechanism coupled to the hook body, the locking mechanism being configured to securely fix the hook anchor to the fixation rod.

2. The hook anchor of claim 1, wherein at least a portion of an interior surface of the hook body is concave so that a first side ridge is formed along a first edge of the interior surface of the hook body and a second side ridge is formed along a second edge of the interior surface of the hook body and wherein the first side ridge runs a length of the interior surface of the hook body so that the first side ridge is shaped in the logarithmic spiral and the second side ridge runs the length of the interior surface of the hook body so that the second side ridge is shaped in the logarithmic spiral.

3. The hook anchor of claim 2, wherein the interior surface of the hook body at a first end of the hook body includes a projection extending towards an interior of the hook body.

4. The hook anchor of claim 1, wherein the locking mechanism is removably coupled to the hook body.

5. The hook anchor of claim 4, wherein the locking mechanism is coupled to the hook body by a threaded connection.

6. The hook anchor of claim 4, wherein the hook body includes a plurality of locking mechanism mount points and the locking mechanism is configured to be selectively coupled to each locking mechanism mount point of the plurality of locking mechanism mount points.

7. The hook anchor of claim 1, wherein a length of the hook body is between 60 millimeters and 70 millimeters.

8. The hook anchor of claim 7, wherein a width of the hook body is between 8 millimeters and 20 millimeters.

9. The hook anchor of claim 8, wherein a thickness of the hook body is between 3 millimeters and 5 millimeters.

10. The hook anchor of claim 1, wherein the hook body includes titanium, titanium alloy, stainless steel, ceramic, and/or a polymer.

11. The hook anchor of claim 1, wherein the hook body is configured to engage a portion of bone that includes at least one of a rib, a pelvis, and a vertebra.

12. The hook anchor of claim 11, wherein the hook body is configured to engage with at least one of a spinous process a transverse process, and a pedicle of the vertebra.

13. A spine stabilization system, comprising:
a fixation rod;
a first hook anchor, including:
    a first hook body shaped in a curve, wherein the curve is a first closed logarithmic spiral and a first rotation vector defining a radius of curvature at a first end of the curve is rotated by at least 270 degrees from a second rotation vector defining a second radius of curvature at a second end of the curve, and
    a first locking mechanism coupled to the first hook body, the first locking mechanism being configured to securely fix the first hook anchor to the fixation rod at a first location on the fixation rod; and
a second hook anchor, including:
    a second hook body shaped in a second curve, wherein the second curve is a second closed logarithmic spiral and a first rotation vector defining a radius of curvature at a first end of the curve is rotated by at least 270 degrees from a second rotation vector defining a second radius of curvature at a second end of the curve, and
    a second locking mechanism coupled to the second hook body, the second locking mechanism being configured to securely fix the second hook anchor to the fixation rod at a second location on the fixation rod.

14. The spine stabilization system of claim 13, wherein:
the first locking mechanism is removably coupled to the first hook body; and
the second locking mechanism is removably coupled to the second hook body.

\* \* \* \* \*